US008632608B2

(12) United States Patent
Carpentier et al.

(10) Patent No.: US 8,632,608 B2
(45) Date of Patent: Jan. 21, 2014

(54) TREATMENT OF BIOPROSTHETIC TISSUES TO MITIGATE POST IMPLANTATION CALCIFICATION

(75) Inventors: Sophie M. Carpentier, Paris (FR); Alain F. Carpentier, Paris (FR)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 13/352,027

(22) Filed: Jan. 17, 2012

(65) Prior Publication Data

US 2012/0117734 A1 May 17, 2012

Related U.S. Application Data

(60) Continuation of application No. 10/992,563, filed on Nov. 18, 2004, now abandoned, which is a division of application No. 10/039,367, filed on Jan. 3, 2002, now Pat. No. 6,878,168.

(51) Int. Cl.
A61L 27/00 (2006.01)
A61L 27/14 (2006.01)
A61L 27/34 (2006.01)

(52) U.S. Cl.
USPC .......................... 8/94.11; 623/11.11; 422/36

(58) Field of Classification Search
USPC ................... 623/11.11; 8/94.11; 422/336, 36
See application file for complete search history.

(56) References Cited

U.S. PATENT DOCUMENTS

| 2,393,580 | A | 1/1946 | Weiskopf |
| 2,484,813 | A | 10/1949 | Bower |
| 2,567,929 | A | 9/1951 | Fessenden |
| 3,002,895 | A | 10/1961 | Freedman |
| 3,093,439 | A | 6/1963 | Bothwell |
| 3,870,789 | A | 3/1975 | Mikat |
| 3,927,422 | A | 12/1975 | Sawyer |
| 3,961,097 | A | 6/1976 | Gravlee, Jr. |
| 3,966,401 | A | 6/1976 | Hancock et al. |
| 4,050,893 | A | 9/1977 | Hancock et al. |
| 4,067,091 | A | 1/1978 | Backman |
| 4,082,507 | A | 4/1978 | Sawyer et al. |
| 4,120,649 | A | 10/1978 | Schechter |
| 4,120,991 | A | 10/1978 | Ornstein et al. |
| 4,197,658 | A | 4/1980 | Fraser |
| 4,207,689 | A | 6/1980 | Romera-Sierra et al. |
| 4,294,753 | A | 10/1981 | Urist |
| 4,320,157 | A | 3/1982 | von Hagens |
| 4,323,358 | A | 4/1982 | Lentz et al. |
| 4,328,256 | A | 5/1982 | Romero-Sierra et al. |
| 4,347,671 | A | 9/1982 | Dias et al. |
| 4,350,492 | A | 9/1982 | Wright et al. |
| 4,372,743 | A | 2/1983 | Lane |
| 4,378,224 | A | 3/1983 | Nimni et al. |
| 4,402,697 | A | 9/1983 | Pollock et al. |
| 4,405,327 | A | 9/1983 | Pollock |
| 4,481,009 | A | 11/1984 | Nashef |
| 4,553,974 | A | 11/1985 | Dewanjee |
| 4,599,084 | A | 7/1986 | Nashef |
| 4,624,822 | A | 11/1986 | Arru et al. |
| 4,647,283 | A | 3/1987 | Carpentier et al. |
| 4,648,881 | A | 3/1987 | Carpentier et al. |
| 4,655,773 | A | 4/1987 | Grassi |
| 4,676,070 | A | 6/1987 | Linner |
| 4,729,139 | A | 3/1988 | Nashef |
| 4,753,652 | A | 6/1988 | Langer et al. |
| 4,770,665 | A | 9/1988 | Nashef |
| 4,776,853 | A | 10/1988 | Klement et al. |
| 4,786,287 | A | 11/1988 | Nashef et al. |
| 4,800,603 | A | 1/1989 | Jaffe |
| 4,831,065 | A | 5/1989 | Pietsch et al. |
| 4,838,888 | A | 6/1989 | Nashef |
| 4,865,871 | A | 9/1989 | Livesey et al. |
| 4,885,005 | A | 12/1989 | Nashef et al. |
| 4,891,319 | A | 1/1990 | Roser |
| 4,911,713 | A | 3/1990 | Sauvage et al. |
| 4,958,008 | A | 9/1990 | Petite et al. |
| 4,969,912 | A | 11/1990 | Kelman et al. |

(Continued)

FOREIGN PATENT DOCUMENTS

WO WO 84/01894 5/1984
WO WO 95/11047 4/1995

(Continued)

OTHER PUBLICATIONS

Carpenter, A., et al., "Biological Factors Affecting Long-Term Results of Valvular Heterografts," Forty-ninth Meeting of the American Association for Thoracic Surgery, San Francisco, CA, Mar. 31-Apr. 2, 1969.
Chanda, J., et al., "Heparin in Calcification Prevention of Porcine Pericardial Bioprostheses," Biomaterials, Elsevier Science Publishers, vol. 18, No. 16, ISSN: 0142-9612, Aug. 1, 1997.
Khora, Eugene, "Methods for the Treatment of Collagenous Tissues for Bioprostheses," Biomaterials, vol. 18, Issue 2, Jan. 1997, pp. 95-105.
Jayakrishnan, A., et al., "Glutaraldehyde as a Fixative in Bioprostheses and Drug Delivery Matrices," Biomaterials, vol. 17, Issue 5, 1996, pp. 471-484.

(Continued)

*Primary Examiner* — Lorna M Douyon
*Assistant Examiner* — Amina Khan
(74) *Attorney, Agent, or Firm* — AnneMarie Kaiser

(57) ABSTRACT

Bioprosthetic tissues are treated by immersing or otherwise contacting fixed, unfixed or partially fixed tissue with a glutaraldehyde solution that has previously been heat-treated or pH adjusted prior to its contact with the tissue. The prior heat treating or pH adjustment of the glutaraldehyde solution causes its free aldehyde concentration to decrease by about 25% or more, preferably by as much as 50%, and allows a "stabilized" glutaraldehyde solution to be obtained at the desired concentration and pH for an optimal fixation of the tissue at high or low temperature. This treatment results in a decrease in the tissue's propensity to calcify after being implanted within the body of a human or animal patient.

21 Claims, 2 Drawing Sheets

(56) References Cited

U.S. PATENT DOCUMENTS

| | | | |
|---|---|---|---|
| 4,975,526 | A | 12/1990 | Kuberasampath et al. |
| 4,976,733 | A | 12/1990 | Girardot |
| 4,990,131 | A | 2/1991 | Dardik et al. |
| 4,994,030 | A | 2/1991 | Glowczewskie, Jr. et al. |
| 4,994,237 | A | 2/1991 | Login et al. |
| 4,996,054 | A | 2/1991 | Pietsch et al. |
| 5,002,566 | A | 3/1991 | Carpentier et al. |
| 5,011,913 | A | 4/1991 | Benedict et al. |
| 5,024,830 | A | 6/1991 | Linner |
| 5,044,165 | A | 9/1991 | Linner et al. |
| 5,051,401 | A | 9/1991 | Sikes |
| 5,068,086 | A | 11/1991 | Sklenak et al. |
| 5,068,100 | A | 11/1991 | McClanahan |
| 5,080,670 | A | 1/1992 | Imamura et al. |
| 5,094,661 | A | 3/1992 | Levy et al. |
| 5,104,405 | A | 4/1992 | Nimni |
| 5,108,923 | A | 4/1992 | Benedict et al. |
| 5,116,564 | A | 5/1992 | Jansen et al. |
| 5,131,908 | A | 7/1992 | Dardik et al. |
| 5,147,514 | A | 9/1992 | Mechanic |
| 5,149,621 | A | 9/1992 | McNally et al. |
| 5,149,653 | A | 9/1992 | Roser |
| 5,154,007 | A | 10/1992 | Piunno et al. |
| 5,200,399 | A | 4/1993 | Wettlaufer et al. |
| 5,215,541 | A | 6/1993 | Nashef et al. |
| 5,275,954 | A | 1/1994 | Wolfinbarger et al. |
| 5,279,612 | A | 1/1994 | Eberhardt |
| 5,290,558 | A | 3/1994 | O'Leary et al. |
| 5,296,583 | A | 3/1994 | Levy |
| 5,332,475 | A | 7/1994 | Mechanic |
| 5,336,616 | A | 8/1994 | Livesey et al. |
| 5,368,608 | A | 11/1994 | Levy et al. |
| 5,397,353 | A | 3/1995 | Oliver et al. |
| 5,424,047 | A | 6/1995 | Zwingenberger et al. |
| 5,436,291 | A | 7/1995 | Levy et al. |
| 5,437,287 | A | 8/1995 | Phillips et al. |
| 5,447,536 | A | 9/1995 | Giradot et al. |
| 5,447,724 | A | 9/1995 | Helmus et al. |
| 5,460,962 | A | 10/1995 | Kemp |
| 5,476,516 | A | 12/1995 | Seifter et al. |
| 5,507,813 | A | 4/1996 | Dowd et al. |
| 5,509,932 | A | 4/1996 | Keogh et al. |
| 5,558,379 | A | 9/1996 | Wehner |
| 5,558,875 | A | 9/1996 | Wang |
| 5,595,571 | A | 1/1997 | Jaffe et al. |
| 5,613,982 | A | 3/1997 | Goldstein |
| 5,632,778 | A | 5/1997 | Goldstein |
| 5,645,587 | A | 7/1997 | Chanda et al. |
| 5,674,298 | A | 10/1997 | Levy et al. |
| 5,679,112 | A | 10/1997 | Levy et al. |
| 5,695,729 | A | 12/1997 | Chow et al. |
| 5,697,972 | A | 12/1997 | Kim et al. |
| 5,720,777 | A | 2/1998 | Jaffe et al. |
| 5,733,339 | A | 3/1998 | Giradot et al. |
| 5,746,775 | A | 5/1998 | Levy et al. |
| 5,762,600 | A | 6/1998 | Bruchman et al. |
| 5,766,520 | A | 6/1998 | Bronshtein |
| 5,769,780 | A | 6/1998 | Hata et al. |
| 5,773,285 | A | 6/1998 | Park |
| 5,776,182 | A | 7/1998 | Bruchman et al. |
| 5,782,914 | A | 7/1998 | Schankereli |
| 5,782,915 | A | 7/1998 | Stone |
| 5,782,931 | A | 7/1998 | Yang et al. |
| 5,792,603 | A | 8/1998 | Dunkelman et al. |
| 5,843,180 | A | 12/1998 | Jaffe et al. |
| 5,843,181 | A | 12/1998 | Jaffe et al. |
| 5,843,182 | A | 12/1998 | Goldstein |
| 5,855,620 | A | 1/1999 | Bishopric et al. |
| 5,856,102 | A | 1/1999 | Bierke-Nelson et al. |
| 5,856,172 | A | 1/1999 | Greenwood et al. |
| 5,862,806 | A | 1/1999 | Cheung |
| 5,865,849 | A | 2/1999 | Stone |
| 5,873,812 | A | 2/1999 | Ciana et al. |
| 5,879,383 | A | 3/1999 | Bruchman et al. |
| 5,882,850 | A | 3/1999 | Khor et al. |
| 5,882,918 | A | 3/1999 | Goffe |
| 5,899,936 | A | 5/1999 | Goldstein |
| 5,902,338 | A | 5/1999 | Stone |
| 5,904,718 | A | 5/1999 | Jefferies |
| 5,911,951 | A | 6/1999 | Giradot et al. |
| 5,913,900 | A | 6/1999 | Stone |
| 5,919,472 | A | 7/1999 | Trescony et al. |
| 5,922,027 | A | 7/1999 | Stone |
| 5,931,969 | A * | 8/1999 | Carpentier et al. ............ 8/94.11 |
| 5,935,168 | A | 8/1999 | Yang et al. |
| 5,945,319 | A | 8/1999 | Keogh |
| 5,977,153 | A | 11/1999 | Camiener |
| 5,987,720 | A | 11/1999 | Yamamoto |
| 5,993,844 | A | 11/1999 | Abraham et al. |
| 6,008,292 | A | 12/1999 | Lee et al. |
| 6,017,741 | A | 1/2000 | Keogh |
| 6,024,735 | A | 2/2000 | Wolfinbarger, Jr. |
| 6,063,120 | A | 5/2000 | Stone |
| 6,066,160 | A | 5/2000 | Colvin et al. |
| 6,093,204 | A | 7/2000 | Stone |
| 6,093,530 | A | 7/2000 | McIlroy et al. |
| 6,106,555 | A | 8/2000 | Yang |
| 6,117,979 | A | 9/2000 | Hendriks et al. |
| 6,121,041 | A | 9/2000 | Mirsch, II et al. |
| 6,132,473 | A | 10/2000 | Williams et al. |
| 6,132,986 | A | 10/2000 | Pathak et al. |
| 6,156,531 | A | 12/2000 | Pathak et al. |
| 6,166,184 | A | 12/2000 | Hendriks et al. |
| 6,177,514 | B1 | 1/2001 | Pathak et al. |
| 6,190,407 | B1 | 2/2001 | Ogle et al. |
| 6,193,749 | B1 | 2/2001 | Schroeder et al. |
| 6,203,755 | B1 * | 3/2001 | Odland ......................... 422/22 |
| 6,206,917 | B1 | 3/2001 | Williams et al. |
| 6,210,957 | B1 | 4/2001 | Carpentier et al. |
| 6,214,054 | B1 | 4/2001 | Cunanan et al. |
| 6,214,055 | B1 | 4/2001 | Simionescu et al. |
| 6,231,608 | B1 | 5/2001 | Stone |
| 6,231,614 | B1 | 5/2001 | Yang |
| 6,251,579 | B1 | 6/2001 | Moore et al. |
| 6,254,635 | B1 | 7/2001 | Schroeder et al. |
| 6,258,320 | B1 | 7/2001 | Persing et al. |
| 6,267,786 | B1 | 7/2001 | Stone |
| 6,277,555 | B1 | 8/2001 | Duran |
| 6,287,338 | B1 | 9/2001 | Sarnowski et al. |
| 6,290,991 | B1 | 9/2001 | Roser et al. |
| 6,302,909 | B1 | 10/2001 | Ogle et al. |
| 6,312,474 | B1 | 11/2001 | Francis et al. |
| 6,322,593 | B1 | 11/2001 | Pathak et al. |
| 6,322,994 | B1 | 11/2001 | Reid |
| 6,328,762 | B1 | 12/2001 | Anderson et al. |
| 6,352,708 | B1 | 3/2002 | Duran et al. |
| 6,364,905 | B1 | 4/2002 | Simpson et al. |
| 6,372,228 | B1 | 4/2002 | Gregory |
| 6,375,680 | B1 | 4/2002 | Carlyle |
| 6,376,244 | B1 | 4/2002 | Atala |
| 6,383,732 | B1 | 5/2002 | Stone |
| 6,391,538 | B1 | 5/2002 | Vyavahare et al. |
| 6,394,096 | B1 | 5/2002 | Constantz |
| 6,448,076 | B2 | 9/2002 | Dennis et al. |
| 6,468,660 | B2 | 10/2002 | Ogle et al. |
| 6,471,723 | B1 | 10/2002 | Ashworth et al. |
| 6,479,079 | B1 | 11/2002 | Pathak et al. |
| 6,506,339 | B1 | 1/2003 | Giradot et al. |
| 6,509,145 | B1 | 1/2003 | Torrianni |
| 6,527,979 | B2 | 3/2003 | Constantz et al. |
| 6,531,310 | B1 | 3/2003 | Mirsch, II et al. |
| 6,534,004 | B2 | 3/2003 | Chen et al. |
| 6,547,827 | B2 | 4/2003 | Carpentier et al. |
| 6,561,970 | B1 | 5/2003 | Carpentier et al. |
| 6,569,200 | B2 | 5/2003 | Wolfinbarger, Jr. et al. |
| 6,582,464 | B2 | 6/2003 | Gabbay |
| 6,586,006 | B2 | 7/2003 | Roser et al. |
| 6,586,573 | B1 | 7/2003 | Besman et al. |
| 6,589,591 | B1 | 7/2003 | Mansouri et al. |
| 6,605,667 | B1 | 8/2003 | Badejo et al. |
| 6,613,278 | B1 | 9/2003 | Mills et al. |
| 6,617,142 | B2 | 9/2003 | Keogh et al. |
| 6,630,001 | B2 | 10/2003 | Duran et al. |
| 6,652,594 | B2 | 11/2003 | Francis et al. |

(56) References Cited

U.S. PATENT DOCUMENTS

| | | |
|---|---|---|
| 6,653,062 B1 | 11/2003 | DePablo et al. |
| 6,660,265 B1 | 12/2003 | Chen |
| 6,685,940 B2 | 2/2004 | Andya et al. |
| 6,696,074 B2 | 2/2004 | Dai et al. |
| 6,734,018 B2 | 5/2004 | Wolfinbarger, Jr. et al. |
| 6,753,181 B2 | 6/2004 | Atala |
| 6,790,229 B1 | 9/2004 | Berreklouw |
| 6,797,000 B2 | 9/2004 | Simpson et al. |
| 6,828,310 B2 | 12/2004 | Barresi et al. |
| 6,878,168 B2 | 4/2005 | Carpentier et al. |
| 6,893,666 B2 | 5/2005 | Spievack |
| 6,908,591 B2 | 6/2005 | MacPhee et al. |
| 6,919,172 B2 | 7/2005 | DePablo et al. |
| 6,933,326 B1 | 8/2005 | Griffey et al. |
| 7,008,763 B2 | 3/2006 | Cheung |
| 7,063,726 B2 | 6/2006 | Crouch et al. |
| 7,078,163 B2 | 7/2006 | Torrianni |
| 7,087,723 B2 | 8/2006 | Besman et al. |
| 7,318,998 B2 | 1/2008 | Goldstein et al. |
| 7,338,757 B2 | 3/2008 | Wolfinbarger, Jr. et al. |
| 7,354,749 B2 | 4/2008 | Fisher et al. |
| 7,358,284 B2 | 4/2008 | Griffey et al. |
| 7,594,974 B2 | 9/2009 | Cali et al. |
| 7,648,676 B2 | 1/2010 | Mills et al. |
| 2001/0000804 A1 | 5/2001 | Goldstein et al. |
| 2001/0020191 A1 | 9/2001 | Williams et al. |
| 2001/0025196 A1 | 9/2001 | Chinn et al. |
| 2001/0032024 A1 | 10/2001 | Cunanan et al. |
| 2001/0039459 A1 | 11/2001 | Stone |
| 2002/0001834 A1 | 1/2002 | Keogh et al. |
| 2002/0111532 A1 | 8/2002 | Pathak et al. |
| 2003/0035843 A1 | 2/2003 | Livesey et al. |
| 2003/0125805 A1 | 7/2003 | Johnson et al. |
| 2003/0135284 A1 | 7/2003 | Crouch et al. |
| 2003/0167089 A1 | 9/2003 | Lane |
| 2004/0030381 A1 | 2/2004 | Shu |
| 2004/0086543 A1 | 5/2004 | Keogh et al. |
| 2004/0158320 A1 | 8/2004 | Simionescu et al. |
| 2004/0193259 A1 | 9/2004 | Gabbay |
| 2005/0079200 A1 | 4/2005 | Rathenow et al. |
| 2005/0119736 A1 | 6/2005 | Zilla et al. |
| 2005/0136510 A1 | 6/2005 | Hendriks et al. |
| 2006/0099326 A1 | 5/2006 | Keogh et al. |
| 2006/0110370 A1 | 5/2006 | Pathak |
| 2006/0159641 A1 | 7/2006 | Giradot et al. |
| 2006/0177426 A1 | 8/2006 | Gibson et al. |
| 2006/0210960 A1 | 9/2006 | Livesey et al. |
| 2006/0217804 A1 | 9/2006 | Dove |
| 2006/0217805 A1 | 9/2006 | Dove |
| 2007/0050014 A1 | 3/2007 | Johnson |
| 2007/0292459 A1 | 12/2007 | Cooper et al. |
| 2008/0302372 A1 | 12/2008 | Davidson et al. |
| 2009/0041729 A1 | 2/2009 | Wolfinbarger, Jr. et al. |

FOREIGN PATENT DOCUMENTS

| | | |
|---|---|---|
| WO | WO 95/22361 | 8/1995 |
| WO | WO 95/34332 | 12/1995 |
| WO | WO 96/04028 | 2/1996 |
| WO | WO 96/13227 | 5/1996 |
| WO | WO 00/32252 | 6/2000 |
| WO | WO 03/037227 | 5/2003 |
| WO | WO 2004/082536 | 9/2004 |
| WO | WO 2006/099334 | 9/2006 |

OTHER PUBLICATIONS

Dahm, Manfred, et al., "Effects of Surface Seeding with Vital Cells on the Calcium Uptake of Biological Materials for Heart Valve Replacement," J Heart Valve Dis, vol. 5, No. 2, Mar. 1996, 148-151.

R Parker, et al. Storage of Heart Valve Allografts in Glycerol With Subsequent Antibiotic Sterilisation, Thorax, 1978, 638-645, vol. 33:5, British Thoracic Society, London, UK.

Zilla, P., et al., "Carbodiimide Treatment Dramatically Potentiates the Anticalcific Effect of Alpha-Amino Oleic Acid on Glutaraldehyde-Fixed Aortic Wall Tissue," The Annals of Thoracic Surgery, Elsevier, vol. 79, No. 3, ISSN: 0003-4975; Mar. 1, 2005.

* cited by examiner

TREATMENT OF BIOPROSTHETIC TISSUES TO MITIGATE POST IMPLANTATION CALCIFICATION

RELATED APPLICATIONS

The present application is a continuation of U.S. patent application Ser. No. 10/992,563, filed Nov. 18, 2004, now abandoned, which is a divisional of U.S. patent application Ser. No. 10/039,367, filed Jan. 3, 2002, now U.S. Pat. No. 6,878,168, both of which are expressly incorporated herein by reference.

FIELD OF THE INVENTION

This invention pertains generally to biomaterials and more particularly to methods for mitigating the post-implantation calcification of bioprosthetic materials and the bioprosthetic devices and articles produced by such methods.

BACKGROUND OF THE INVENTION

Implantable biological tissues can be formed of human tissues preserved by freezing (i.e., cryopreserving) the so called homograft tissues, or of animal tissues preserved by chemically fixing (i.e., tanning) the so called bioprosthesis (Carpentier, Biological Tissues in Heart Valve Replacement, Butterworth (1972), Ionescu editor). The type of biological tissues used as bioprostheses include cardiac valves, blood vessels, skin, dura mater, pericardium, small intestinal submucosa ("SIS tissue"), ligaments and tendons. These biological tissues typically contain connective tissue proteins (i.e., collagen and elastin) that act as the supportive framework of the tissue. The pliability or rigidity of each biological tissue is largely determined by the relative amounts of collagen and elastin present within the tissue and/or by the physical structure and configuration of its connective tissue framework. Collagen is the most abundant connective tissue protein present in most tissues. Each collagen molecule is made up of three (3) polypeptide chains intertwined in a coiled helical configuration.

The techniques used for chemical fixation of biological tissues typically involve the exposure of the biological tissue to one or more chemical fixatives (i.e., tanning agents) that form cross-linkages between the polypeptide chains within a given collagen molecule (i.e., intramolecular crosslinkages), or between adjacent collagen molecules (i.e., intermolecular crosslinkages).

Examples of chemical fixative agents that have been utilized to crosslink collagenous biological tissues include: formaldehyde, glutaraldehyde, dialdehyde starch, hexamethylene diisocyanate and certain polyepoxy compounds. Of the various chemical fixatives available, glutaraldehyde has been the most widely used since the discovery of its antiimmunological and antidegenerative effects by Dr. Carpentier in 1968. See Carpentier, A., J. Thorac. Cardiovascular Surgery, 58: 467-69 (1969). In addition, glutaraldehyde is one of the most efficient sterilization agents. Glutaraldehyde is used as the fixative and the sterilant for many commercially available bioprosthetic products, such as porcine bioprosthetic heart valves (e.g., the Carpentier-Edwards® stented porcine Bioprosthesis), bovine pericardial heart valves (e.g., Carpentier-Edwards® Pericardial Bioprosthesis) and stentless porcine aortic valves (e.g., Edwards PRIMA Plus® Stentless Aortic Bioprosthesis), all manufactured and sold by Edwards Lifesciences LLC, Irvine, Calif.

One problem associated with the implantation of many bioprosthetic materials is that the connective tissue proteins (i.e., collagen and elastin) within these materials can become calcified following implantation within the body. Such calcification can result in undesirable stiffening or degradation of the bioprosthesis. Two (2) types of calcification—intrinsic and extrinsic—are known to occur in fixed collagenous bioprostheses. Intrinsic calcification follows the adsorption by the tissue of lipoproteins and calcium binding proteins. Extrinsic calcification follows the adhesion of cells (e.g., platelets) to the bioprosthesis and leads to the development of calcium phosphate containing surface plaques on the bioprosthesis.

The factors that affect the rate at which fixed tissue bioprostheses undergo calcification have not been fully elucidated. However, factors thought to influence the rate of calcification include the patient's age, the existence of metabolic disorders (i.e., hypercalcemia, diabetes, etc.), dietary factors, the presence of infection, parenteral calcium administration, dehydration, in situ distortion of the bioprosthesis (e.g., mechanical stress), inadequate anticoagulation therapy during the initial period following surgical implantation and immunologic host-tissue responses.

Various techniques have heretofore been proposed for mitigating the in situ calcification of glutaraldehyde-fixed bioprostheses or for otherwise improving the glutaraldehyde fixation process. Included among these are the methods described in U.S. Pat. No. 4,729,139 (Nashef) entitled Selective Incorporation of a Polymer into Implantable Biological Tissue to Inhibit Calcification; U.S. Pat. No. 4,885,005 (Nashef et al.) entitled Surfactant Treatment of Implantable Biological Tissue To Inhibit Calcification; U.S. Pat. No. 4,648,881 (Carpentier et al.) entitled Implantable Biological Tissue and Process For Preparation Thereof; U.S. Pat. No. 4,976,733 (Girardot) entitled Prevention of Prosthesis Calcification; U.S. Pat. No. 4,120,649 (Schechter) entitled Transplants; U.S. Pat. No. 5,002,566 (Carpentier) entitled Calcification Mitigation of Bioprosthetic Implants; EP 103947A2 (Pollock et al.) entitled Method For Inhibiting Mineralization of Natural Tissue During Implantation, and U.S. Pat. No. 5,215,541 (Nashef et al.) entitled Surfactant Treatment of Implantable Biological Tissue to Inhibit Calcification. Recently a new technique of calcium mitigation by high temperature fixation of the tissue in glutaraldehyde has been developed and was described in U.S. Pat. No. 5,931,969 (Carpentier et al.) entitled Methods And Apparatus For Treating Biological Tissue To Mitigate Calcification. Although some of these techniques have proven to be efficient in reducing calcification, there remains a need in the art for further improvements of the existing techniques or for the development of new calcification-mitigating techniques to lessen the propensity for post-implantation calcification of fixed bioprosthetic tissues.

SUMMARY OF THE INVENTION

The present invention provides methods for treating tissue to inhibit post implant calcification whereby fixed, unfixed or partially fixed tissue is immersed in or otherwise contacted with a pre-treated glutaraldehyde solution. In a preferred embodiment of the present invention, the glutaraldehyde solution is heat-treated prior to its contact with the tissue. Preferably, the glutaraldehyde solution is heated to a first temperature for a first period of time. The temperature of the glutaraldehyde solution is then adjusted to a second temperature (preferably lower than the first temperature), before contacting the bioprosthetic tissue.

The first temperature to which the glutaraldehyde solution is heated is sufficiently high, and is maintained for sufficiently long, to cause the free aldehyde content and pH of the glutaraldehyde solution to fall by a predetermined amount. Preferably, the prior heat treating of the glutaraldehyde solution causes the free aldehyde concentration of the solution to decrease by about 25%, preferably by about 50%. The glutaraldehyde solution may be buffered so that the pH is initially in the range of about 7.2 to 7.S, preferably about 7.4. After the heating has been carried out, the pH of the solution will typically have fallen to approximately 5.0 to 7.0, preferably 6.0. Due to the preheating of the glutaraldehyde solution, the solution does not significantly change its chemical characteristics when used to treat the tissue later in the procedure.

In a preferred embodiment, the glutaraldehyde solution is heated to a first temperature of at least 20° C., but preferably not more than 90° C. More preferably, the glutaraldehyde solution is heated to a temperature between about 60° C. to SO° C., and most preferably about 70° C.±5° C. The glutaraldehyde solution may become somewhat yellow in color during this heat-treatment step. The time period during which the first temperature must be maintained will typically vary inversely with the first temperature (Le., lower temperatures will require a longer period of time to cause a decrease in free aldehyde content and/or a fall in pH). Preferably, the glutaraldehyde is heated to the first temperature for a period of time between about one hour and six months, and more preferably about 1 day to 2 months. Thereafter, the solution is filtered and adjusted to a second temperature before adding the tissue. Preferably, this second temperature may be in the range of about 30° C. to 70° C., preferably about 40-60° C., and more preferably about 50° C.±5° C.

In another embodiment of the present invention, glutaraldehyde solution is not heat treated but the pH of the glutaraldehyde solution is adjusted to a pH within the range of about 5.0 to 7.0, and preferably to about 6.0. The pretreated glutaraldehyde solution, whether by preheating or pH adjustment, is then used to treat the tissue, preferably at a temperature in the range of about 30° C. to 70° C., more preferably at a temperature between about 40° C. to 60° C., and most preferably, at a temperature of about 50° C.±5° C. In a preferred embodiment, the tissue is treated for a period of time between about one hour to six months, and more preferably for about one day to two months. For example, at a temperature of about 50° C., the preferred period of time is between about 5 days to 10 days, and most preferably, for about seven days.

The heat-treated or pH adjusted glutaraldehyde solution may, in some cases, also be used as a terminal sterilization solution such that the calcification-decreasing treatment with previously treated glutaraldehyde and a terminal sterilization may be carried out simultaneously with the same solution and/or in a single container.

The heat-treated glutaraldehyde solutions may also contain other chemicals to enhance its efficacy, such as surfactants (e.g., Tween® 80), alcohol (e.g., ethanol) and/or aldehydes (e.g., formaldehyde).

In another embodiment of the method of the present invention, the tissue is heat treated in a preheated solution other than glutaraldehyde, for example, any other fixative solution or a surfactant solution (e.g., Tween® 80 with or without ethanol and/or formaldehyde), or a physiologic solution (e.g., saline or a balanced salt solution). The preheating of the solution is carried out at a temperature between about 20° C. to 90° C., more preferably between about 37° C. and 60° C., and most preferably about 45° C., for one hour to six months, preferably one day to two months. In the preheated solution, the tissue is heat treated between about 30° C. and 70° C., and more preferably about 50° C., for about one day to two months. In another embodiment, the tissue is heat treated in a nonpreheat treated physiologic solution wherein the pH has been adjusted between 5.0 and 7.0, preferably 6.0.

The method of the present invention results in a decrease in the tissue's propensity to calcify after being implanted within the body of a human or animal patient. Prior to, concurrently with, or after undergoing treatment with the pre-treated glutaraldehyde, the tissue may be chemically fixed by exposing the tissue to one or more chemical fixatives or cryopreserved by freezing the tissue in accordance with well known techniques.

Further in accordance with the invention, there are provided bioprosthetic devices or articles that are formed, wholly or partially, of tissue that has been treated in accordance with the various embodiments of the method of the present invention. Examples of biological tissues of human or animal origin which may be used in bioprosthetic devices or articles of the present invention include, but are not necessarily limited to: heart valves; venous valves; blood vessels; ureter; tendon; dura mater; skin; pericardium; cartilage (e.g., meniscus); ligament; bone; intestine (e.g., intestinal wall); small intestinal submucosa ("SIS tissue"), and periostium.

Further in accordance with the present invention, there are provided methods for treating diseases and disorders of mammalian patients, by implanting bioprosthetic materials that have undergone the calcification mitigating treatment of the various embodiments of the method of the present invention. Such treatment methods include, but are not limited to, a) the surgical replacement of diseased heart valves with bioprosthetic heart valves that have been treated with glutaraldehyde in accordance with the present invention, b) the repair or bypassing of blood vessels by implanting biological vascular grafts that have been treated with glutaraldehyde in accordance with the present invention, c) the surgical replacement or repair of torn or deficient ligaments by implanting bioprosthetic ligaments that have been treated with glutaraldehyde in accordance with the present invention and, d) the repair, reconstruction, reformation, enhancement, bulking, ingrowth, reconstruction or regeneration of native tissues by implanting one or more biopolymeric or bioprosthetic tissue scaffolds that have been treated with glutaraldehyde in accordance with the present invention (e.g., tissue engineering with a natural tissue or biopolymeric scaffold).

Still further in accordance with this invention, the various embodiments of the method of mitigating post-implantation calcification of bioprosthetic tissues offer significant advantages over previous practices wherein glutaraldehyde was heated in the presence of the tissue, as the present invention allows the desirable features of the heat treatment to be achieved prior to any contact between the glutaraldehyde solution and the tissue, and also allows the temperature of the glutaraldehyde solution to be lowered to about 30° C. to 70° C., preferably about 40° C. to 60° C., or most preferably at about 50° C. prior to any contact with the tissue. This lessens the potential for untoward or undesirable reactions to the bioprosthetic tissue due to exposure to high free aldehyde concentrations and/or long term heat treatment at temperatures above 60° C. It also allows for treatment of the tissue within realistic manufacturing time frames.

Still further in accordance with this invention, the method of preheating the solution, and/or heating the tissue, offer better sterilization of both the solution and the tissue at the different stages of the manufacturing process, including the terminal stage. Further aspects and advantages of the present invention will become apparent to those skilled in the relevant art, upon reading and understanding the "Description of Exemplary Embodiments" set forth herebelow.

DESCRIPTION OF THE EXEMPLARY EMBODIMENTS

Figure 1:
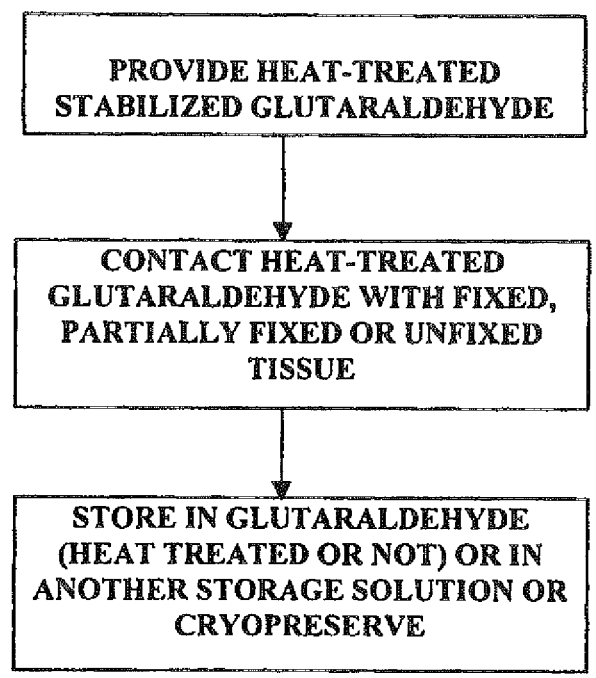
FIG. 1 is a flow diagram of one embodiment of the method for mitigating calcification of a bioprosthetic material, in accordance with the present invention.

The following examples are provided for the purpose of describing and illustrating a few exemplary embodiments of the invention only. One skilled in the art will recognize that other embodiments of the invention are possible, but are not described in detail here. Thus, these examples are not intended to limit the scope of the invention in any way.

It has previously been reported that cross-linked bioprosthetic tissue post-treated in 0.625% glutaraldehyde phosphate solution for 2 months at 50° C., with fluid movement (e.g., shaking), exhibited less calcification in the rat subcutaneous and rabbit intramuscular implant models than control cross-linked bioprosthetic tissue fixed in 0.625% glutaraldehyde phosphate solution under typical conditions (I.e., room temperature for 1-14 days). See 66 Ann. Thoracic Surgery 264-6 (1998). Tissues treated under these conditions exhibited a characteristic tan to brown appearance. The heated 0.625% glutaraldehyde phosphate solution also darkened to an amber-brown color and the aldehyde concentration within that solution dropped to about 0.3%.

Since the above publication, the Applicant has discovered that it is advantageous to conduct the heating step on the glutaraldehyde solution prior to its contact with the tissue. The heat-treated glutaraldehyde may then be cooled to a lower temperature and the tissue may then be added to the cooled glutaraldehyde solution under conditions of reduced severity, greater convenience, or both (e.g., shorter time, lower temperature, or both). By heat-treating the glutaraldehyde solution in the absence of the tissue, higher temperatures, concentrations or both can be used during the heat-treating process without risking or causing any adverse effect on the tissue. In another embodiment, the glutaraldehyde solution can be buffered by adjusting the pH of the solution to within a range of about 5.0 to 7.0, preferably about 6.0. Applicants have found that the buffered glutaraldehyde solution has a similar, although slightly less, advantageous effect as the heat-treated glutaraldehyde solution.

The mechanism by which the heat-treated glutaraldehyde mitigates post-implantation calcification is not presently known with certainty. However, Applicants postulate that this calcification mitigating effect is due at least in part to the leaching of lipoproteins and calcium binding proteins and in part to the formation of a calcification mitigating chemical or moiety within the glutaraldehyde solution that acts to limit or inhibit the fixation of calcium into the tissue, either by way of a physical barrier effect (i.e., by retarding diffusion at the boundary layer) and/or by chemically modifying the structure and the surface charge of the tissue and thus its affinity to attract calcium ions. Heat-treated glutaraldehyde can also be used to enhance sterilization by leaving the tissue in the heat-treated glutaraldehyde or by heating the tissue within the previously heat treated glutaraldehyde solution to temperatures between about 37° C. and 60° C.

A. General Method for Mitigating Calcification of Bioprosthetic Material

FIG. 1 is a flow diagram that generally illustrates one embodiment of the method of the present invention. As shown in FIG. 1, the first step of the process is to heat treat glutaraldehyde solution in the absence of tissue. It will be appreciated that the concentration of glutaraldehyde in the starting solution may be varied. Thereafter, the solution concentration may be adjusted, if desired, prior to addition of the tissue. It is believed that glutaraldehyde concentrations of as little as 0.1% and as much as 25% or more may be used during the heat-treating step. Reduced glutaraldehyde concentrations of 0.6% to 2.5% have, to date, been successfully obtained and used by Applicant, and those skilled in the art will recognize that higher or lower concentrations of glutaraldehyde may indeed prove to be advantageous during the heat-treating step of the process. The preferred concentration for use during the heat-treating step (FIG. 1) is 1.0-2.0%. This heat-treating of the glutaraldehyde may be accomplished by heating of the solution until the free aldehyde content of the solution has fallen about 2S % or more and remains stable at that level (e.g., a solution of 1.8% falls to about 0.6% or less). Initially, the solution containing glutaraldehyde may be buffered to a pH of 7.4 with a phosphate buffer, a non-phosphate buffer such as a HEPES buffer, or other suitable buffered solutions, and, in such cases, heating of the solution to cause the free aldehyde content to fall will also cause the pH of the solution to fall. In another embodiment of the present invention, rather than heat treating the glutaraldehyde solution, the pH may be adjusted from 7.4 to a pH within the range of about 5.0 to 7.0, preferably 6.0.

The heat-treating of the glutaraldehyde may be accomplished by any suitable means. In this example, the glutaraldehyde is pre-heated to and maintained at a temperature between about 20-90° C., preferably between about 60° C.-80° C., and most preferably 70° C.±5° C. for a sufficient period of time to cause the free aldehyde concentration to decrease by at least 2S % and to stabilize at a pH of approximately 6.0 (i.e., the pH of 6.0 corresponds to a free aldehyde concentration of about 0.3-0.7%). Depending on the temperature used, the step of heat treating the glutaraldehyde may take anywhere from one hour to six months or more depending on the temperature used. The preferred method is to heat the glutaraldehyde solution to approximately 70° C.±5° C., for approximately 1 day to 2 months or until the desired fall of at least 2S % or more in free aldehyde concentration and a pH of approximately 6.0, are observed.

After the heat-treatment of the glutaraldehyde has been completed the solution is cooled to a second temperature that does not cause damage to the tissue (e.g., about 30° C. to 70° C., preferably about 40° C. to 60° C., or most preferably at about SO° C.). An unfixed, partially-fixed, or fixed tissue is then contacted with the heat-treated glutaraldehyde. Tissue that has been "fully fixed" in this regard means that the tissue has been fixed to an extent suitable for use as an implant, while "partially fixed" means that the tissue has been fixed to some extent short of being fully fixed. This tissue treatment step is preferably accomplished by immersing fixed, partially fixed or unfixed tissue in the heat-treated glutaraldehyde solution while maintaining the solution at about 30° C. to 70° C., preferably about 40° C. to 60° C., or most preferably at about 50° C. It is preferable that the pH of the solution be left at about 6.0 prior to placement of the tissue within the solution. Thereafter, the temperature of the solution is maintained at approximately 50° C. with the tissue immersed in the solution to allow the heat-treated glutaraldehyde solution to interact with or modify the tissue. The tissue's susceptibility to post-implant calcification will be significantly reduced after immersion for as little as one hour to as much as six months or more (depending primarily on the temperature used), but typically occurs within 1 to 15 days at 50° C.

In another embodiment of the method of the present invention, the tissue may be heat treated in a surfactant solution (e.g., Tween® 80 with or without ethanol and/or formaldehyde) or in a physiologic solution (e.g. saline or a balanced salt solution) at a temperature between about 37° C. and 60° C., preferably about 45° C., for about one hour to six months, preferably about one to 15 days, and then heat treated in a glutaraldehyde solution as described above.

Prior to, concurrently with or after the tissue treatment step, the tissue may be cryopreserved or otherwise preserved, i.e. by fixation.

Figure 2:
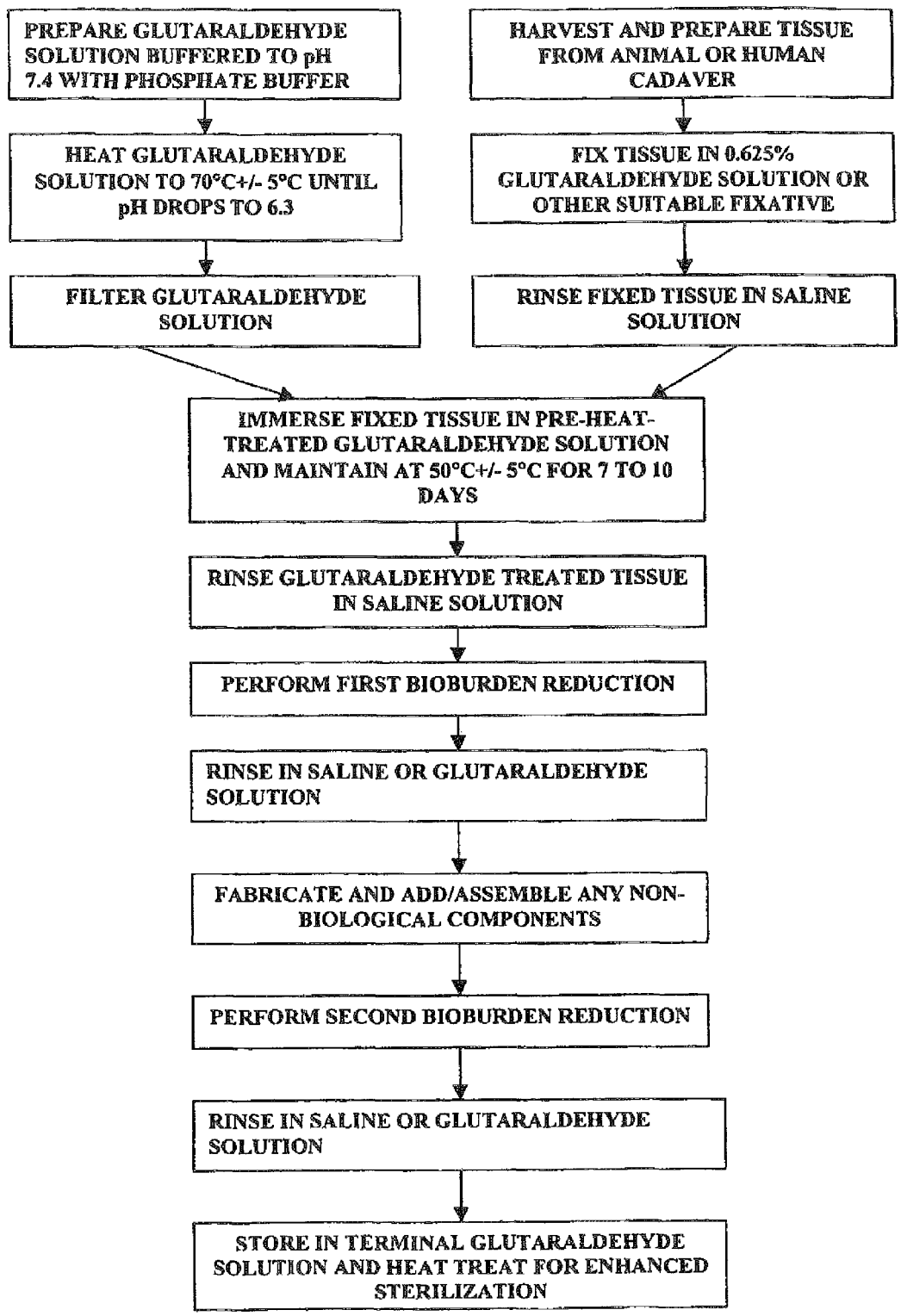
FIG. 2 is a flow diagram of another embodiment of the method for preparing a bioprosthetic device in accordance with the method of the present invention.

B. An Example of a Method for Manufacturing a Fixed Heterologous Heart Valve Bioprosthesis Having Mitigated Propensity for Post-Implantation Calcification FIG. 2 is a flow diagram of a specific process for manufacturing a bioprosthetic device, such as a stented or stentless porcine heart valve or bovine pericardial heart valve of the type referred to herein. The following is a description of the exemplary process shown in FIG. 2.

1. Heat-Treating of Glutaraldehyde

Prepare Glutaraldehyde Solution

Initially, an aqueous solution of 1.8% by weight glutaraldehyde is prepared in a clean, inert vessel (e.g., a vessel made of stainless steel, plastic or borosilicate glass) and such solution is then buffered to the pH of approximately 7.4 by adding phosphate buffered saline solution.

Preheat Glutaraldehyde Solution in Absence of Tissue

The glutaraldehyde in the solution is then preheated. Such preheating of the glutaraldehyde is accomplished by heating of the solution to about 70° C.±SoC and maintaining such temperature until the pH of the solution falls to approximately 6.0. At this point, the color of the solution can be colorless to golden or brown. The fall of the solution pH to 6.0 and the accompanying change in color to golden or brown indicates that the preheating treatment has been completed. This preheating step is typically completed after 1-14 days, preferably 6-8 days, of maintaining the solution at the 70° C.±5° C. temperature. Higher temperatures ranging up to approximately 90° C. may be used, and the use of such higher temperatures will typically speed the desired fall in free aldehyde concentration and accompanying change in pH (e.g., a solution having a starting pH adjusted to 7.4 will fall to a pH of about 6.0 after approximately 1-3 days at 90° C.). Lower temperatures, ranging downward to approximately 20° C., may also be used, and the use of such lower temperatures will typically cause the desired free aldehyde content and pH changes to take longer. After the heat treatment of the solution has been carried out the solution is filtered.

Optional Neutralization of pH of Heat-Treated Glutaraldehyde Solution

After the glutaraldehyde has been heat-treated, the solution is allowed to cool to about SO° C. and its pH may be adjusted at step 24 back to approximately 7.4 by adding phosphate buffered saline or some other suitable buffer.

2. Harvesting, Preparation and Fixation of Tissue:

Harvesting/Preparation of Biological Tissue

The desired biological tissue is harvested from a human cadaver or animal donor, and prepared for subsequent fixation and treatment. The tissue is typically harvested by surgical cutting or removal from its host animal. Thereafter, it is typically trimmed or cut to size and washed with sterile water, basic salt solution, saline or other suitable washing solution.

Fixation of Biological Tissue

The biological tissue may be fixed prior to, during or after its treatment with the heat-treated glutaraldehyde. In this example, the tissue is fixed prior to undergoing the treatment with heat-treated glutaraldehyde. This fixation is carried out by immersing the tissue in a solution of 0.625% by weight glutaraldehyde buffered to a pH of approximately 7.4 by a suitable buffer such as a phosphate buffer, for 1-14 days at ambient temperature. In order to enhance fixation or sterilization other chemical compounds such as surfactants (e.g. Tween® 80) and/or ethanol and/or formaldehyde can be added to the glutaraldehyde. It will be appreciated, however, that various other fixatives may be used, such as aldehydes (e.g., formaldehyde, glutaraldehyde, dialdehyde starch) or polyglycidyl ethers (e.g., Denacol 810), or heterologous bifunctional or multifunctional crosslinkers.

Rinsing of Tissue

After it has been removed from the fixative solution, the tissue is thoroughly rinsed with saline solution, basic salt solution or free glutaraldehyde solution or some other suitable washing solution.

3. Treatment of Tissue with Heat-Treated Glutaraldehyde to Mitigate Post-Implantation Calcification:

Immersion of Tissue in Heat-Treated Glutaraldehyde Solution

After the fixed tissue has been rinsed, it is treated with the pre-heat treated glutaraldehyde solution. The pre-heat treated glutaraldehyde solution is placed in a vessel such as a stainless steel bath, cooled to and maintained at preferably 50° C.±5° C. The fixed/rinsed tissue is then immersed in the heat-treated glutaraldehyde solution and the solution is continually maintained at 50° C.±5° C. with the tissue immersed in the solution with or without fluid movement. The tissue's susceptibility to post-implant calcification will be significantly reduced after immersion for as little as one hour to as much as six months or more (depending primarily on the temperature used), but typically occurs within 6 to 8 days at 50° C.±5°. Thereafter, the tissue is removed from the solution. The tissue is typically brown in color at this time.

Rinsing of Tissue

After it has been removed from the heat-treated glutaraldehyde solution, the tissue is thoroughly rinsed with saline solution, basic salt solution or some other suitable washing solution.

4. Poststerilization, Assembly/Fabrication and Storage of Bioprosthesis

First Bioburden Reduction (BREP I)

After the tissue has been fixed, treated with the heat-treated glutaraldehyde and rinsed, it is subjected to a first bioburden reduction treatment immersed in or otherwise contacted with a mixture containing i) a crosslinking agent, ii) a denaturing agent and iii) a surfactant (i.e., a CDS solution). One preferred CDS solution (described in U.S. Pat. No. 4,885,005 and U.S. Pat. No. 4,648,881) is a mixture of i) formaldehyde, ii) ethanol and ii) surfactant (e.g., Tween® 80 surfactant, available from ICI Americas, Brantford, Ontario). Such preferred CDS solution may also be referred to by the acronym "FETS" and has a preferred formulation as follows:

Formaldehyde 4.0.±.0.4% by weight
Ethanol 22.0.±.2.2% by weight
Tween® 80 1.2.±.0.2% by weight The tissue is preferably immersed in the CDS solution for 2 hours to 7 days and typically about 2 hours. During this immersion period, the CDS solution is maintained at a temperature of 4-50° C., and preferably at about 20-37° C.

Those skilled in the art will appreciate that various alternative chemical compounds or solutions may be substituted for each component of the CDS solution, as follows:

Potential Alternative Crosslinking Agents:

A. Aldehydes: formaldehyde, glutaraldehyde, paraformaldehyde, glyceraldehyde, glyoxal acetaldehyde or acrolein B. Epoxides: any of the various Denacols and their individual reactive species, including mono, di, tri, and multi-functionalized epoxides C. Carbodiimides D. Mixed multifunctional molecules (e.g. aldehyde-epoxide combination)

Potential Alternative Denaturing Agents:

A. Alcohols/Solvents: e.g., ethanol, isopropyl alcohol

B. Acidified Ethers: e.g., sulfuric acid/ether mixture, acetone, ethers of small alkyl size (methyl, ethyl, etc. but probably not beyond butyl)

C. Ketones: e.g., methyl ethyl ketone (MEK)

D. Commercial Solvent Systems: e.g., Genesolve™ (Allied Signal, Inc., Morristown, N.J.)

E. Glycols: glycerol ethylene glycol, polyethylene glycol, low molecular weight carbowax F. Chaotropic Agents: e.g., urea, guanidine hydrochloride, guanidine thiocyanate, potassium iodide G. High Concentration Salt Solutions: e.g., lithium chloride, sodium chloride, cesium chloride.

Potential Alternative Surfactants:

(these surfactant compounds can be used individually or in mixtures such as deoxycholate/Triton or commercially-available mixtures such as Micro-80/90.)

A. Anionic Surfactants: e.g., esters of lauric acid, including but not limited to sodium laurel sulfate (also called sodium dodecyl sulfate)

B. Alkyl sulfonic acid salts: e.g., 1-decanesulfonic acid sodium salt

C. Non-ionic compounds: e.g., compounds based on the polyoxyethylene ether structures, including Triton X-IOO, 114, 405, N-101 (available commercially from Sigma Chemical, St. Louis, Mo.) and related structures; Pluronic and Tetronic surfactants (available commercially from BASF Chemicals, Mount Olive, N.J.)

D. Alkylated Phenoxypolyethoxy Alcohols: e.g., NP40, Nonidet P40, Igepal, CA630, hydrolyzedlfunctionalized animal and plant compounds including Tween® 80, Tween® 20, octyl-derivatives, octyl b-glucoside, octyl bthioglucopyranoside, deoxycholate and derivatives thereof, zwitterionic compounds, 3-([cholamidopropyl]-dimethyl amino)-1-propanesulfonate (CHAPS), 3-([cholamidopropyl]-dimethyl amino)-2-hydroxy-1-propanesulfonat-e (CHAPSO) (available from Pierce Biotec Company, Rockford, Ill.).

Fabrication/Assembly

After the first bioburden reduction has been completed, the tissue maybe again rinsed with a suitable rinsing solution such as isotonic saline or 0.625% glutaraldehyde and transported into a clean room or aseptic environment. Thereafter, the tissue may be further trimmed or shaped (if necessary) and attached to or assembled with any non-biological components (e.g., stents, frames, suture rings, conduits, segments of polyester mesh to prevent suture tear-through, etc.) to form the desired bioprosthetic device. Examples of bioprosthetic devices that are assembled of both biological tissue and non-biological components include stented porcine bioprosthetic heart valves (e.g., the Carpentier-Edwards® Bioprosthesis), and bovine pericardial heart valves (e.g., Carpentier-Edwards® Pericardial Bioprosthesis), stentless porcine aortic valves that incorporate fabric reinforcements (e.g., Edwards PRIMA Plus® Stentless Aortic Bioprosthesis), and conduit valves for bio-mechanical ventricular assist devices (e.g., the Novacor N-100PC model), all available from Edwards Lifesciences LLC, Irvine, Calif.

Second Bioburden Reduction (BREP II)

After the bioprosthesis has been fabricated and assembled it is subjected to a second bioburden reduction that is essentially a repeat of the first bioburden reduction described above, however, in this second bioburden reduction step, the solution is preferably maintained at about 37° C. for approximately 2 hours to 10 days, preferably about 9 hours.

Terminal Heating and Storage

After completion of the second bioburden reduction, the tissue (or bioprosthesis) is rinsed with a suitable rinsing solution (such as isotonic saline or 0.625% glutaraldehyde solution) and then" placed in a terminal solution for storage and sterilization. The preferred terminal solution is a glutaraldehyde solution having a concentration of about 0.2 to 1.0% by weight glutaraldehyde, and most preferably about 0.625% by weight glutaraldehyde. This solution has a strong sterilizing effect that can be enhanced by a terminal heating of the solution.

In this terminal sterilization step, the tissue (or bioprosthesis) is immersed in or contacted with the terminal solution and heated for a period of time sufficient to ensure sterility of the bioprosthesis until the time of implantation. The period of heating varies depending upon the temperature utilized, i.e., the lower the temperature the longer the period of time. For example, from 1 or 2 hours to 1 month for temperatures between about 50° C. and 20° C., respectively. Preferably, the period of time is 1 to 6 days at 37° C. or 6 hours to 2 days at 50° C., but one of skill in the art will recognize that these temperature or time values can be modified within the scope of the invention.

In order to avoid additional transfer and manipulation, the terminal heating is preferably carried out in the sealed storage container or package in which the bioprosthesis will be shipped and stored until the time of implantation. The tissue (or bioprosthesis) is aseptically deposited in the storage container that has been pre-filled with the 0.625% glutaraldehyde aqueous solution buffered to a pH of 7.4 with sodium hydroxide, such that the tissue (or bioprosthesis) is fully immersed in the buffered glutaraldehyde solution. Thereafter, the container is sealed and placed at room temperature for at least 7 days, or in an oven at 37° C. for 24 hours, or at 50° C. for 6 hours to enhance the sterilization power of glutaraldehyde. Thereafter, the container is cooled to room temperature and shipped to the hospital or other location(s) where it is stored until the time of use of the bioprosthesis.

In another embodiment, the terminal heating is carried out before placing the tissue or bioprosthesis in the storage container.

In some cases, glutaraldehyde that has been heat-treated in accordance with this invention may be used as the terminal solution and, in such cases, it may be possible to shorten or completely eliminate the previous step of immersing the tissue in previously heat-treated glutaraldehyde, opting instead to accomplish some or all of the treatment of the tissue by heat-treated glutaraldehyde until the last step of storage, i.e., concurrently with the terminal sterilization step.

While the foregoing is a complete description of the preferred embodiments of the invention, various alternatives, modifications, and equivalents may be used. Moreover, it will be obvious that certain other modifications may be practiced within the scope of the appended claims.

What is claimed is:

1. A method for mitigating post-implantation calcification of a bioprosthetic implant tissue, said method comprising the steps of:

obtaining biological tissue;

exposing the tissue to a fixation process to form cross-linkages in the tissue to obtain a fixed tissue;

providing a starting solution selected from the group consisting of a glutaraldehyde solution and a physiologic solution;

adjusting the pH of the starting solution to a pH of 6.0 without heating the starting solution;

immersing a quantity of the fixed tissue in the pH-adjusted solution; and heating the pH-adjusted solution and the fixed tissue to a heat treating temperature in the range of about 30° C. to 70° C. for a period of time.

2. The method of claim 1, wherein the heat treating temperature is in the range of about 40° C. to 60° C.

3. The method of claim 1, wherein the heat treating temperature is about 50° C.±5° C.

4. The method of claim 1, wherein the period of time is between about one hour and six months.

5. The method of claim 1, wherein the period of time is between about one day and two months.

6. The method of claim 1, wherein the period of time is between about 5 days to 10 days.

7. The method of claim 1, wherein the period of time is about 7 days.

8. The method of claim 1, wherein the starting solution is aqueous glutaraldehyde buffered to a starting pH, wherein the step of adjusting comprises lowering the pH.

9. The method of claim 8, wherein the starting pH is between about 7.2 to 7.8.

10. The method of claim 1, wherein the bioprosthetic implant material is a bioprosthetic heart valve, and the method further comprises the steps of:

harvesting the biological tissue from a human cadaver or animal donor; preparing the tissue by trimming to size and washing with a suitable washing solution; and assembling the heat treated and fixed tissue with non-biological components to form a bioprosthetic heart valve.

11. The method of claim 10, wherein the heat treating temperature is in the range of about 40° C. to 60° C.

12. The method of claim 10, wherein the heat treating temperature is about 50° C.±5° C.

13. The method of claim 10, wherein the period of time is between about one day and two months.

14. The method of claim 10, wherein the period of time is between about 5 days to 10 days.

15. The method of claim 10, wherein the period of time is about 7 days.

16. The method of claim 10, further including, after the tissue has been fixed and heat treated, and prior to assembly into a heart valve, subjecting the fixed tissue to a first bioburden reduction process including:

contacting the fixed tissue with a mixture containing:
  i) a crosslinking agent,
  ii) a denaturing agent and
  iii) a surfactant.

17. The method of claim 16, further including, after assembling the heart valve, subjecting the fixed tissue to a second bioburden reduction process including:

contacting the fixed tissue with a mixture containing:
  i) a crosslinking agent,
  ii) a denaturing agent and
  iii) a surfactant.

18. The method of claim 17, wherein the second bioburden reduction process is done at a temperature of about 37° C. for a period of time longer than the first bioburden reduction process.

19. The method of claim 18, further including storing the heart valve in a solution of glutaraldehyde.

20. The method of claim 10, wherein the starting solution is aqueous glutaraldehyde buffered to a starting pH, wherein the step of adjusting comprises lowering the pH.

21. The method of claim 20, wherein the starting pH is between about 7.2 to 7.8.

* * * * *